United States Patent [19]

Bahia et al.

[11] Patent Number: 5,731,083

[45] Date of Patent: Mar. 24, 1998

[54] CELLULOSIC FIBRES

[75] Inventors: Hardev Singh Bahia, Coventry; Jim Robert James, Bedworth, both of United Kingdom

[73] Assignee: Courtaulds PLC, United Kingdom

[21] Appl. No.: 568,266

[22] Filed: Dec. 6, 1995

Related U.S. Application Data

[63] Continuation of Ser. No. 244,644, filed as PCT/GB92/02283, Dec. 9, 1992, abandoned.

[30] Foreign Application Priority Data

Dec. 9, 1991 [GB] United Kingdom ............. 9126193

[51] Int. Cl.[6] ..................................... B32B 23/00
[52] U.S. Cl. .................. 428/393; 428/359; 428/364; 428/378; 428/396; 8/115.51; 8/116.1; 8/121; 427/307; 427/308; 427/324; 604/358; 604/365; 604/374; 604/376; 442/197; 442/416
[58] Field of Search .................. 428/359, 364, 428/378, 393, 394, 396; 8/115.51, 116.1, 181, 196; 427/307, 308, 324; 264/194, 195, 207; 604/358, 365, 374, 375, 376

[56] References Cited

U.S. PATENT DOCUMENTS

| | | |
|---|---|---|
| 1,736,714 | 11/1929 | Lilienfeld . |
| 3,563,241 | 2/1971 | Evans et al. . |
| 3,589,364 | 6/1971 | Dean et al. . |
| 3,723,413 | 3/1973 | Chatterjee et al. . |
| 3,731,680 | 5/1973 | Wright et al. . |
| 3,731,686 | 5/1973 | Chatterjee . |
| 3,847,636 | 11/1974 | Smith . |
| 3,858,585 | 1/1975 | Chatterjee . |
| 4,044,766 | 8/1977 | Kaczmarzyk et al. . |
| 4,200,557 | 4/1980 | Chatterjee et al. . |
| 4,246,221 | 1/1981 | McCorsley . |
| 4,405,324 | 9/1983 | Cruz . |
| 4,410,694 | 10/1983 | Nakayama et al. . |
| 4,538,603 | 9/1985 | Pawelchak et al. . |
| 4,579,943 | 4/1986 | Kamide et al. . |
| 4,651,725 | 3/1987 | Kifune et al. . |
| 4,728,642 | 3/1988 | Pawelchak et al. . |
| 5,197,945 | 3/1993 | Cole et al. . |

FOREIGN PATENT DOCUMENTS

| | | |
|---|---|---|
| 3209126 | 10/1982 | Germany . |
| 49-055993 | 5/1974 | Japan . |
| 56-015458 | 2/1981 | Japan . |
| 3000825 | 1/1991 | Japan . |
| 3269144 | 11/1991 | Japan . |
| 2094802 | 9/1982 | United Kingdom . |
| 2220881 | 1/1990 | United Kingdom . |

OTHER PUBLICATIONS

D. Perrier et al, "Properties of Carboxymethylated Cotton Prepared in Nonaqueous Media", *Journal of Applied Polymer Science*, 17:3375–3389 (1973) [Perrier I].

D. Perrier et al, "Catalysis of the Cellulose–Cyclic Urea Reactions by Built–In Acid Groups", *Textile Research Journal*, pp. 680–685 (1971) [Perrier II].

*Primary Examiner*—Patrick Ryan
*Assistant Examiner*—J. M. Gray
*Attorney, Agent, or Firm*—Howson and Howson

[57] ABSTRACT

Carboxymethyl cellulose fiber having a degree of substitution of at least 0.1, preferably 0.2–0.5, carboxymethyl groups per glucose unit is derived from solvent-spun cellulose fiber, for example by reaction with a strong alkali and a monochloroacetate reagent. The fiber has an absorbency of at least 8 grams, usually at least 15 grams, 0.9% saline solution per gram of fibre and a tenacity of at least 10, usually at least 15, cN/tex. It can be used for absorbent personal products.

16 Claims, No Drawings

CELLULOSIC FIBRES

This is a continuation of application Ser. No. 08/244,644, filed as GB92/02283, Dec. 9, 1992, now abandoned.

FIELD OF THE INVENTION

This invention relates to cellulosic fibres having high absorbency for aqueous fluids. Such fibres are used in absorbent personal products, such as disposable diapers, tampons, sanitary napkins and incontinence pads, and in absorbent wipes, and may also be used as part of the fibre content in moisture-absorbing clothing or in towels. The absorbency of cellulosic fibres can be increased by incorporating highly absorbent chemicals in the fibres or by chemical modification of the cellulose itself. The incorporation of highly absorbent chemicals has the risk that the chemicals may be released from the fibres. The present invention is concerned with chemically modified cellulosic fibres, in particular carboxymethylated cellulose fibres.

BACKGROUND ART

Carboxymethyl cellulose in powder form is well known commercially as a thickener. It is produced by reaction of cellulose pulp with a strong alkali such as sodium hydroxide and monochloroacetic acid or a salt thereof. There have been several suggestions for the production of carboxymethyl cellulose fibres but these have not been widely used commercially. Documents describing the production of carboxymethyl cellulose fibres are GB-A-2220881, GB-A-2094802, U.S. Pat. No. 3731680, U.S. Pat. No. 736714, JP-A-49-55993, JP-A-56-15458, JP-A-3-825 and JP-A-3-269144, and articles in J. Applied Polymer Science, volume 17 (1973) at pages 3375–3388 and Textile Research J., 1971, pages 680–685. The references describe the production of carboxymethyl cellulose fibres from regenerated cellulose (viscose rayon) fibres or from cotton. There are problems in achieving highly absorbent fibres which are free of surface stickiness and which are strong enough to be processed on textile machinery.

DISCLOSURE OF THE INVENTION

We have found according to the invention that carboxymethyl cellulose fibre of greater absorbency and strength free from surface stickiness can be produced from solvent-spun cellulose fibre.

Carboxymethyl cellulose fibre according to the invention has a degree of substitution of at least 0.1 carboxymethyl group per glucose unit and is characterised in that the fibre is derived from solvent-spun cellulose fibre and has an absorbency of at least 8 grams 0.9% saline solution per gram of fibre, as measured by the free swell method, and a tenacity of at least 10 cN/tex.

A process according to the invention for the production of carboxymethyl cellulose fibre by reacting cellulose fibre with a strong alkali and a monochloroacetic reagent selected from monochloroacetic acid and salts thereof is characterised in that the cellulose fibre used is solvent-spun cellulose fibre.

Solvent-spun cellulose fibres are fibres spun from a solution of cellulose in a solvent, as opposed to regenerated cellulose fibres which are spun from a solution of a cellulose derivative (cellulose xanthate) which is reconverted to cellulose in the bath into which the fibres are spun. Examples of solvents for cellulose are tertiary amine N-oxides, N,N-dimethyl formamide/nitrogen tetroxide mixtures, dimethyl sulphoxide/paraformaldehyde mixtures and solutions of lithium chloride in N,N-dimethyl acetamide or N-methyl pyrrolidone. The preferred solvents for use in producing solvent-spun cellulose fibres are tertiary amine N-oxides. The production of solvent-spun cellulose fibres is described for example in U.S. Pat. No. 4,246,221 and U.S. Pat. No. 4,196,281, which give examples of preferred tertiary amine N-oxides. The solution of cellulose is spun through an air gap into a bath of a non-solvent for cellulose, usually water, where the cellulose is precipitated in fibre form.

Solvent-spun cellulose fibre has two main differences in structure from regenerated cellulose fibre and cotton. It has a substantially uniform structure across its cross-section and has greater crystallinity. Regenerated cellulose and cotton fibres both have a structure which includes a relatively dense skin at the surface of the fibre. Solvent-spun cellulose fibre has no such skin. We believe that either or both of these properties is important in producing carboxymethyl cellulose fibres of high absorbency without weakening the fibre during the carboxymethylation process to such an extent that it loses its fibre structure.

When carrying out the process of the invention the alkali and the monochloracetic reagent can be applied to the cellulose fibre simultaneously or sequentially. The cellulose fibre can be in the form of a tow, yarn, staple fibre or fabric, for example a woven, knitted or non-woven fabric. If a non-woven fabric is used, it is preferably one in which the fibres are relatively securely bound in the fabric, for example a hydroentangled or needled fabric. The yarn, tow or fibre can be a blend of the cellulose fibre with one or more other fibres such as polyester or nylon which are unaffected by the carboxymethylation process. In the case of tow, yarn or staple fibre the fibre can be dry fibre as commercially sold or it can be never-dried fibre, that is fibre which has not been dried after fibre formation. The rate of uptake of reagents by the fibre and the rate of reaction with the cellulose of the fibre may be somewhat faster using never-dried fibre. If never-dried fibre is used, its water content is preferably controlled to be less than 150%, for example 50 to 100%, by weight by mangling if necessary.

The alkali and the monochloroacetic compound are preferably applied from aqueous solution. The alkali is preferably an alkali metal hydroxide such as sodium hydroxide or potassium hydroxide and is preferably used at a concentration of at least 2% by weight, more preferably 4% or 5% or more, up to 15% by weight, more preferably up to 10%. The monochloroacetic acid is preferably used in salt form, usually the salt corresponding to the alkali used, for example sodium monochloroacetate with sodium hydroxide. The monochloroacetic reagent is preferably used at a concentration of at least 5% by weight, more preferably at least 10%, up to 35% by weight, more preferably up to 25%. The alkali and monochloroacetate salt are preferably used in approximately equimolar amounts, for example at a molar ratio of 0.8–1.2:1. Sodium hydroxide and sodium monochloroacetate are preferably used at a weight ratio of 1:2.5–3.5, most preferably about 1:2.9. If monochloroacetic acid is used, the molar ratio of alkali to monochloroacetic acid is preferably about 2:1.

The alkali and the monochloroacetic reagent can be applied from solution in a mixture of water and a polar organic solvent. For example, sodium hydroxide can be dissolved in water at up to 35% by weight and sodium monochloroacetate dissolved in water at up to 45% by weight, and the solutions can be mixed and diluted with an alcohol such as ethanol or industrial methylated spirits to give the required concentration of reagents in the aqueous organic solvent mixture.

Various procedures can be used for applying the alkali and monochloroacetic reagents to the fibre. The fibre can be immersed in a solution of a reagent at elevated temperature, for example at least 50° C. up to the boiling point of the solution. When the fibre is in the form of a continuous textile material such as a tow or a fabric, the reagent can be applied by padding followed by drying at an elevated temperature. The alkali and monochloroacetic reagents can be applied sequentially, in which case it is preferred but not essential that the alkali is applied before the monochloroacetic reagent, or they can be applied together in a single solution. The padding procedure has the advantage that drying can take place at higher temperatures, allowing shorter reaction time. The drying temperature can, for example, be in the range 50° to 200° C. Drying temperatures of above 100° C. allow reaction times of for example 2 to 10 minutes compared to 4 to 30 minutes for reactions carried out at below 100° C. The amount of liquid taken up during padding is preferably 50 to 300% by weight; the tow or fabric can be squeezed, for example by mangling, after padding if required to give the desired take-up. Too high a liquid level may mean that the time required for drying is greater than the time required for the carboxymethylation reaction. Although still effective, this is wasteful of energy. Care should be taken to avoid substantial weakening of the cellulose fibre by thermal degradation. The most preferred reaction temperatures may be in the range 80° to 150° C., particularly temperatures of 90° C. and above such as 90° to 120° C. The heating of the treated fibres should preferably not be such as to completely dry the fibres, a moisture content of 5 to 20% by weight after drying being preferred. This avoids brittleness of the dried fibres. Heating can take place in an oven or in a hot tunnel dryer in a continuous process.

One example of a procedure for carrying out the process of the invention comprises padding the fibre with alkali, for example aqueous sodium hydroxide, and drying at a temperature above 80° C., followed by treatment with the monochloroacetic reagent, for example sodium monochloroacetate. The alkali-treated fibre can be immersed in an aqueous solution at 50° to 100° C. for 15 to 60 minutes, followed by drying. Alternatively, the sodium monochloroacetate solution can be applied by padding, followed by a drying step at a temperature above 80° C. for 5 to 15 minutes. The fibre in tow or fabric form can be mangled after padding with the sodium hydroxide or after padding with the sodium monochloroacetate, or both, to reduce the liquid take-up on the fibre in each case. If the fibre is mangled to reduce the liquid take-up, the concentration of the solution used should be increased to give a similar level of reagent on fibre. The order of treatment can be reversed, that is the fibre can be padded with sodium monochloroacetate solution and optionally mangled and dried, followed by padding with sodium hydroxide, optionally mangling and drying. In either case, care should be taken when making up the second treatment solution in a continuous process to allow for reagent from the first treatment solution carried by the fibre into the second treatment solution and re-dissolved.

Alternatively, the sodium hydroxide and sodium monochloroacetate can be applied simultaneously. The simultaneous application of sodium hydroxide and sodium monochloroacetate may be preferred because only one drying step is used and the overall reaction time is reduced. A solution containing the required concentration of sodium hydroxide and sodium monochloroacetate can be prepared by mixing the solutions of these reagents which have been separately prepared or by dissolving sodium hydroxide in a solution of sodium monochloroacetate. The mixed solution can be applied by immersion or by padding, optionally followed by mangling, and drying at elevated temperature. The solution containing both sodium hydroxide and sodium momochloroacetate should preferably not be held for an extended time at an elevated temperature, since reaction of the NaOH and ClCH$_2$COONa to form sodium chloride and sodium glycollate can take place. The sodium hydroxide and sodium monochloroacetate solutions can be mixed just before application to the fibre, or the separate solutions can simultaneously be sprayed onto the fibre, for example by sprays arranged at right angles to each other. if the mixed solution of alkali (eg sodium hydroxide) and monochloroacetic reagent (eg sodium monochloroacetate) has to be stored, it is preferably held at a temperature of 20° C. or below, for example 0° to 5° C. Storage at 20°–40° C. of fibre treated with both the alkali and the monochloroacetate is preferably avoided. It is usually most convenient to heat the fibre immediately after padding to effect the carboxymethylation reaction. Alternatively, the padded fibre can be stored at a temperature below 20° C., preferably in the range 0° to 5° C., before heating. It may be preferred to carry out padding at a temperature below 20° C., for example 0° to 10° C.

The degree of substitution of the cellulose fibres achieved is preferably at least 0.15 carboxymethyl group per glucose unit, and is most preferably in the range 0.2 to 0.5. Higher degrees of substitution than 0.5 carboxymethyl group per glucose unit may lead to fibres which are water-soluble rather than water-swellable. Higher degrees of substitution within the above range may be preferred when the fibre is to be used in absorbent products, and lower degrees of substitution within this range may be preferred when the fibre is to be used in garments.

The presence of polyvalent cations, particularly polyvalent metal ions, in at least one reagent solution may be advantageous. Preferred metal ions are calcium ions, but barium, magnesium or zinc are alternatives. We have found that the presence of polyvalent metal ions during processing helps to avoid the formation of fibres which are water-soluble in distilled or demineralised water; it is believed that the polyvalent metal ion may be forming cross-links between carboxylic acid groups on different cellulose chains. The concentration of polyvalent metal salt, for example calcium salt, in the treatment solution can for example be in the range 0.01 to 10% by weight. in many cases, calcium ions present in hard tap water may have a sufficient effect. In other cases it may be preferred to add a calcium salt such as calcium chloride to the treatment solution, for example in an amount of 1 to 4% by weight. In general, the higher the degree of substitution of the cellulose fibre with carboxymethyl groups, the higher is the preferred concentration of calcium ions (within the stated range) in the reagent solution to avoid forming fibres which are soluble in distilled or demineralised water. The polyvalent metal ions, for example calcium ions, can alternatively be applied during washing of the treated fibre by including them in the washing liquid, but this is less effective.

In a modification of the process of the invention, the fibre is first treated with aqueous strong alkali so that the alkali is absorbed throughout the fibre. The fibre is then rinsed with a solvent for the alkali, preferably water, without washing thoroughly. The water may optionally contain one or more surfactants. The effect of such rinsing is to remove more alkali from the outer region of the fibre than from the interior. The fibre is then treated with the monochloroacetic reagent, preferably monochloroacetic acid, and is heated to cause carboxymethylation and drying of the fibre. The level of carboxymethylation is greater at the interior of the fibre where more alkali remains than at the outer regions of the fibre. A rinsing step can be carried out after treatment with the monochloroacetic reagent and before heating and drying; this tends to increase the difference in the degree of carboxymethylation between the interior and the outer regions of the fibre.

The product of this modified process, namely a carboxymethylated cellulose fibre having a higher degree of carboxymethylation at the interior of the fibre than in the outer regions of the fibre, feels similar to conventional cellulosic fibres even when wet but has an increased absorbency.

After the carboxymethylation process, the fibre is usually washed to remove any unreacted alkali or chloroacetate or any by-products such as sodium chloride or sodium glycollate. An aqueous wash is generally used, preferably a mixture of water with a water-miscible organic solvent. The washing medium may contain an organic hydroxyl compound, a surfactant, and/or an acid. The organic hydroxyl compound is a compound containing at least one alcoholic hydroxyl group, for example ethanol, methanol or another low molecular weight alcohol and/or a polyhydroxy compound such as ethylene glycol or propylene glycol. The weight ratio of the organic hydroxyl compound to water can for example be in the range 3:1 to 1:50. A low molecular weight mono-alcohol can act both as water-miscible organic solvent and as organic hydroxyl compound; for example a preferred washing medium is based on a mixture of water and ethanol in weight ratio 2:1 to 1:2. If a surfactant is used it is preferably a non-ionic surfactant such as a polyalkylene oxide adduct of an alcohol or phenol, although anionic or cationic surfactants can be used. Any surfactant used should preferably be hydrophiltc rather than hydrophobic; such a hydrophobic surfactant may reduce the rate of water uptake by the fibres. Examples of preferred surfactants are those sold under the Trade Marks Tween 20surfactant and Atlas G1086surfactant. An acid used during washing to neutralise the alkalinity of the carboxymethylated fibre is preferably a weak acid, for example an organic carboxylic acid such as acetic acid which is used for example at 0.5 to 15% by weight, preferably 1 to 5%. The weight ratio of wash liquor to fibre used during washing is preferably in the range 5:1 to 50:1.

Washing is preferably carried out by a counter-current washing procedure, for example in 2 or 3 stages. In a 2-stage counter-current washing procedure, fibre which has already been washed once is washed again with clean wash liquor. The washed fibre from this second wash stage can be dried for further processing. The liquor resulting from this second wash stage passes to the first wash stage as the wash liquor for unwashed fibre. Counter-current washing allows the use of a lower wash liquor to fibre weight ratio, for example a ratio of 10:1 can be used to wash as effectively as a ratio of 20:1 used in a single washing step. A relatively low concentration of acid, for example 0.5 to 2.0% by weight, can be used in the wash liquor.

As an alternative to inclusion of a surfactant in the wash liquor, it may be preferred to apply a surfactant subsequently as a finish. The surfactant can for example be applied as a solution in an alcohol or an aqueous alcohol mixture, for example the mixture used to wash the fibre, or a liquid surfactant can be applied undiluted. The finish can be applied by immersion of the fibre in the finish, or by lick roller or by spray. If the surfactant is applied as a finish, the fibre is preferably pressed to remove excess wash liquor, for example by mangling, before applying the finish.

After the required washes, the fibre is generally dried. Excess wash liquor is preferably removed by pressure, for example by mangling, followed by heat drying. The optimum degree to which the fibre should be dried depends on the intended further processing, but a moisture content of 5–20% by weight is generally preferred to avoid brittleness of the dried fibres, particularly when drying a tow, yarn or staple fibre which has to undergo further processing such as crimping, carding, weaving or felting.

The treated fibre can be crimped, and it may be preferred to crimp the fibre to give increased loft, particularly if the fibre is to be used in non-woven applications for absorbent products. A tow can for example be crimped by stuffer box crimping. False twist crimping can alternatively be used. If the fibre is to be crimped, it may be possible to omit the heat drying step after washing and to allow the fibre to become dried during crimping.

Carboxymethylated fibre produced from solvent-spun cellulose according to the invention has higner absorbency and superior physical properties compared to carboxymethylated fibre produced from regenerated cellulose or cotton fibres. The absorbency of 0.9% saline solution, as measured by the free-swell method, can for example be 15 or more, e.g. 20 to 40, grams per gram, combined with a tenacity in the range 25–15 cN/tex. Viscose rayon or cotton fibres carboxymethylated by the same process have absorbencies only in the range 8–13 g/g and a lower tenacity. At this level of absorbency, carboxymethylated viscose rayon in particular and carboxymethylated cotton to a lesser extent become sticky on the surface in contact with moisture, so that when a tow of fibres is carboxymethylated the fibres become glued together and lose their individual fibrous nature. This problem is not encountered with the fibres of the present invention, which can be processed using conventional textile machinery, for example by the staple route including cutting, carding and if desired crimping, drafting and spinning. Even at lower degrees of substitution giving lower absorbency, the carboxymethylated solvent-spun cellulose fibres are substantially stronger than carboxymethylated viscose rayon fibres.

The form of the carboxymethylated fibres after swelling in water or in an aqueous liquid such as saline solution depends on the absorbency of the fibres and the diameter of the fibres. Absorbency generally increases with increasing carboxymethyl group content. At high levels of absorbency the swollen fibres tend to form a coherent gel in which the identity of individual fibres is lost, particularly if the fibres are of low decitex. For example, fibres of initial decitex 1.7 per filament and having an absorbency (0.9% saline solution, free swell) of 28 g/g, corresponding to treatment with 19.2% by weight $ClCH_2COONa$ and 6.5% NaOH, swell to a gel in tap water of hardness 400 p.p.m. $CaCO_3$. Fibres of the same initial decitex, treated with 13.3% $ClCH_2COONa$ and 4.5% NaOH and having an absorbency of 20, remain as discrete fibres when swollen in tap water and can be re-dried to fibrous form. Fibres of initial decitex 6.0, treated with 22.1% $ClCH_2COONa$ and 7.5% NaOH and having a absorbency of 27, also remain as discrete fibres when swollen in tap water. For absorbent disposable products, gel formation on swelling is acceptable. For non-disposable garments, retention of fibrous formwhen wet and re-dried is necessary.

The carboxymethylated fibre of the present invention can be used in various products. It can, for example, be used in absorbent personal products such as tampons, disposable diapers, sanitary napkins or incontinence pads. The carboxymethylated fibres are preferably used in combination with one or more other textile fibres, preferably consisting wholly or mainly of cellulosic fibres, for example cellulosic fibres such as cotton or regenerated cellulose or fibres having a higher absorbency than most textile fibres but less than carboxymsuch acellulose fibres, such as multi-limbed cellulose fibres as described in EP-A-301874. The carboxymethylated fibres are preferably intimately mixed with said other fibres, for example by carding or air-laying the fibres together to form a web of mixed fibres, or they can be used as a layer, for example a non-woven fabric, of carboxymethylated fibres sandwiched between layers of said other fibres. The proportion of carboxymethylated fibres in a blend with cellulosic fibres for absorbent products can for example be at least 5% and up to 95%, preferably at least 10% and up to 50%, particularly 15–25%, by weight. The carboxymethylated fibres can also be used at similar levels in conjunction with fluffed wood pulp in absorbent products. Carboxymethylated fibres can be used alone in absorbent personal products, particularly those having a relatively low degree of substitution and relatively low absorbency, but it is preferred to use a blend of carboxymethylated fibres having a relatively high degree of substitution and absorbency with non-carboxymethylated cellulose fibres. The carboxymethylated cellulose fibre of the invention, particularly that having a relatively low degree of substitution, can be used in garments such as underwear or sportswear to give increased absorbency and comfort. For such uses, the carboxymethyl cellulose fibre is usually blended with another fibre, preferably a cellulose fibre such as viscose rayon, including multi-limbed viscose, or cotton, but alternatively a synthetic fibre such as polypropylene or polyester.

The fibre described above having a higher degree of carboxymethylation at the interior of the fibre than in the outer regions is also suitable for use in garments such as underwear or sports wear. It is less effective than uniformly carboxymethylated fibre in absorbent products since its rate of uptake of aqueous fluid is lower, as is its overall absorbency.

A woven fabric or strong non-woven fabric such as a needled or hydroentangled fabric formed of solvent-spun cellulose fibre can be carboxymethylated to form a fabric which swells on contact with water to form a liquid-proof barrier and which can be used for example for wrapping electrical components. A yarn or fabric tape of the carboxymethyl cellulose fibre of the invention can be used to wrap cable or can be laid longitudinally in the cable to prevent water ingress.

The carboxymethyl cellulose fibre of the invention can be used as an absorbent for materials such as camphor or menthol or for perfumes, for example in devices adapted to give slow release of these materials. Slow release of camphor or menthol may be desired for medical uses. Slow release of perfume may be desired in air-freshening devices.

The carboxymethyl cellulose fibre of the invention having a relatively low degree of substitution can be used in papermaking, helping to form strong bonds between fibres on drying.

The carboxymethyl cellulose fibre can be used as an absorbent fibre in many other uses, for example in filters, in absorbent liners or mats for packaging, disposable wipes, shoe insoles, swellable gaskets or seals, moisture retention mats in horticulture, moisture-retaining packaging or swellable self-sealing stitching threads.

The invention is illustrated by the following Examples, in which parts and percentages are by weight:

EXAMPLE 1

Sodium hydroxide and sodium monochLoroacetate were separately dissolved in water and the solutions were cooled to 18° C. The solutions were mixed to form a treatment solution containing 8.5% NaOH and 22.1% $ClCH_2COONa$. A tow of 1.7 decitex solvent-spun cellulosic fibres, the fibres having a substantially uniform structure across their cross-section, as sold under the Trade Mark TENCEL fibres, was padded with the treatment solution for 2 minutes and mangled to give a pick-up (increase in weight of wet fibres) of about 150%. The treated tow was dried at 180° C. for 4 minutes, during which time reaction of the cellulose of the fibres to form sodium carboxymethyl cellulose took place. The dried tow was washed with a solution containing 50% ethanol (industrial alcohol), 35% water, 5% glycerol and 10% acetic acid, and was re-dried.

The tow produced had a degree of substitution in excess of 0.1, a tenacity of 24.8 cN/tex and an extensibility of 15.5%. It absorbed 39 grams tap water (hardness 460 p.p.m. $CaCO_3$) per gram of fibre when allowed to swell freely. The fibres dissolved at least partially in distilled or demineralised water and could not be used as an absorbent for these purified waters; in practical use the fluids being absorbed are generally tap water or aqueous fluids richer in minerals than tap water. The absorbency of the tow for 0.9% saline solution would be somewhat less than for tap water but would be above 20 grams per gram of fibre.

The free swell absorbency was measured by dispersing 0.5 g fibre in 30 ml water and leaving it for 5 minutes. For all absorbency measurements, the fibre is conditioned at 65% relative humidity and 20° C. before being tested. The dispersion is then filtered through a sintered Mark 1 funnel of pore size 100–160 microns and is left for 5 minutes, or until it stops dripping. The water filtered through the funnel is weighed and the weight of water absorbed by the fibres is calculated by subtraction.

EXAMPLES 2 and 3

The procedure of Example 1 was repeated using different times and temperatures for drying the treated tow (reaction times and temperatures). In both cases the degree of substitution was above 0.1 and the tenacity above 10 cN/tex. The results were as follows:

| Example No | Temperature of Drying | Time of Drying | Free Swell Absorbency in Tap Water |
|---|---|---|---|
| 2 | 80° C. | 10 minutes | 44 g/g |
| 3 | 57° C. | 26 minutes | 28 g/g |

EXAMPLES 4 and 5

The procedure of Example 1 was repeated using different concentrations of reagents in the treatment solution. In both cases the degree of substitution was above 0.1. The results obtained were as follows:

| Example No | Concentration of Reagent NaOH | Concentration of Reagent $ClCH_2COONa$ | Tenacity (cN/tex) | Extensibility | Absorbency (Free swell) in tap water |
|---|---|---|---|---|---|
| 4 | 4.0% | 10.4% | 30.6 | 11.8% | 8.7 g/g |
| 5 | 6.5% | 16.9% | 24.9 | 11.3% | 25 g/g |
| Untreated fibres | — | — | 38.0 | 14.0% | 3.5 g/g |

-continued

| | Concentration of Reagent | | Tenacity | Extensi- | Absorb-ency (Free swell) in tap |
|---|---|---|---|---|---|
| Example No | NaOH | ClCH$_2$COONa | (cN/tex) | bility | water |

(The free swell absorbency of the product of Example 4 in 0.9% saline solution was about 8 g/g.)

EXAMPLES 6 and 7

The procedure of Example 1 was repeated except that calcium chloride was added to the tap water used to prepare the solutions of sodium hydroxide and sodium monochloroacetate. The concentration of calcium chloride was 2% (Example 6) and 3% (Example 7). The free swell absorbency in tap water of the tow produced was 33 g/g and 28 g/g respectively. The tenacity was above 20 cN/tex and the degree of substitution above 0.1 in both cases.

EXAMPLE 8

A tow of 1.7 decitex solvent-spun cellulosic fibres was padded with an 8.5% aqueous solution of NaOH to give a pick-up of about 250%. The treated tow was dried at 180° C. for 8 minutes. The tow was then immersed in a 22.1% aqueous solution of ClCH$_2$COONa at 80° C. for 30 minutes. The tow was washed and dried as described in Example 1. The properties of the fibres produced were similar to those of the fibres of Example 2.

EXAMPLE 9

A tow of 1.7 decitex solvent-spun cellulosic fibres was padded with a 22.1% aqueous solution of ClCH$_2$COONa and mangled to give a pick-up of about 150%. The treated tow was dried at 180° C. for 4 minutes. The tow was then padded with an 8.5% aqueous solution of NaOH and mangled to give a pick-up of about 150%. The treated tow was again dried at 180° C. for 4 minutes. The dried tow was washed and dried as described in Example 1.

EXAMPLE 10

The process of Example 9 was repeated except that the order of treatment was reversed; the tow was first treated with sodium hydroxide and then with sodium monochloroacetate.

The fibres produced in Example 9 and in Example 10 each had properties similar to the fibres of Example 1.

EXAMPLE 11

A tow of TENCEL fibres having a filament decitex of 1.7 was obtained in a never-dried state. The tow was passed through a hand mangle. The amount of water left on the tow after mangling was 62%. This wet tow was put in a solution containing 7.5% sodium hydroxide and 22.1% sodium monochloroacetate at room temperature (20° C.) for 2 minutes. The padded tow was mangled again. The total pick-up after mangling was 75%. The padded and mangled tow was then reacted in a conditioning cabinet set at 23% RH (relative humidity) and 90° C. for five minutes. The amount of water retained on the tow after the treatment was 13%.

After heat treatment the tow was washed in a solution containing 55% industrial alcohol, 42% water and 3% acetic acid. Washed tow was then treated with a finish containing 99% industrial alcohol and 1% ATLAS G1086 emulsifier. After this, the tow was dried at a low temperature, leaving some residual moisture on the fibres. The finished tow was crimped using a stuffer box system. The crimped fibres were cut into staple.

The fibres had a degree of substitution above 0.1, a tenacity of 22.5 cN/tex and an extensibility of 12%. The moisture regain of fully dried fibres at 65% RH was 17%. The free swell absorbency of the fibres was measured by the process of Example 1 but using 0.9% saline solution in place of water. The absorbency was 30 g/g. The retention of the saline solution after application of pressure at about 3.4 kPa for 5 minutes or until dripping stops was also measured by weighing the water expressed after application of pressure. The absorbency retention of the fibres was 20 g/g.

COMPARATIVE EXAMPLES

A. The procedure of Example 11 was repeated using a tow of FIBRO regenerated cellulose (viscose rayon) of the same filament decitex. The carboxymethylated viscose rayon fibres produced had a free swell absorbency in 0.9% saline solution of 11 g/g, with a retention of 9 g/g after application of pressure. The carboxymethylated viscose rayon fibres, unlike the carboxymethylated solvent-spun cellulose fibres, became sticky on the surface after brief contact with water.

B. The procedure of Example 11 was also repeated using combed cotton yarn. The carboxymethylated cotton had a free swell absorbency of 10.5 g/g and a retention of 9 g/g after application of pressure.

EXAMPLES 12 to 15

A tow of never-dried TENCEL fibres of filament decitex 1.7 was padded with a solution of sodium hydroxide and sodium monochloroacetate. The concentrations of the reagents differed in different Examples as shown below. The tow was lightly mangled to stop dripping and the total pick-up was measured. The tow was then dried at 90° C. to a moisture level of 13%.

The resulting tow was washed in a solution containing 55% ethanol, 42% water, 2.5% acetic acid and 0.5% citric acid. The washed tow was treated with a finish and dried as described in Example 11. The free swell absorption of the fibres in 0.9% saline solution was measured, as was the retention under 3.42 kPa. The degree of substitution (number of carboxymethyl groups per glucose unit) was also measured. The results were as follows:

| Example No. | Concentration of Reagents % NaOH | Concentration of Reagents % ClCH$_2$COONa | Pick-up % | Degree of Substitution | Free Swell Absorbency g/g | Retention g/g | State of Swollen Fibre |
|---|---|---|---|---|---|---|---|
| 12 | 4.5 | 13.3 | 200 | 0.235 | 20 | 10 | Fibrous |
| 13 | 5.5 | 16.2 | 230 | 0.29 | 18 | 10 | Fibrous |
| 14 | 6.5 | 19.2 | 230 | 0.375 | 28 | 18 | Gel |
| 15 | 7.5 | 22.1 | 275 | 0.405 | 38 | 29 | Gel |

The tenacity of the fibres reduced with increasing degree of substitution but was in all cases greater than 15cN/tex.

EXAMPLES 16 and 17

The process of Example 15 was repeated using samples of solvent-spun cellulosic fibre tows of different filament decitex. The results obtained were as follows:

| Example No. | Initial filament decitex | Pick up % | Tenacity cN/tex | Extensibility % | Free Swell Absorbency g/g | Retention g/g | State of swollen fibre |
|---|---|---|---|---|---|---|---|
| 16 | 3.0 | 265 | 25.6 | 17.7 | 31 | 22 | Gel |
| 17 | 6.0 | 273 | 18.8 | 17.7 | 27 | 17 | Fibrous |

EXAMPLES 18 to 20

15% carboxymethylated fibres produced according to the invention were carded in a blend with 85% multi-limbed regenerated cellulose fibres, sold under the trade mark GALAXY fibres, using a SHIRLEY Miniature Card. The carboxymethylated fibres used were:

Example 18 crimped fibres produced according to Example 11

Example 19 fibres produced according to Example 11 omitting the crimping stage

Example 20 crimped fibres produced according to Example 15.

The carded webs were each formed into a radially expanding tampon and tested for absorbency in a "modified Syngina" test as defined in GB-A-2094637, pages 4 to 6, except that a 200 mm hydrostatic head air pressure was employed. The absorbency in the modified Syngina test was tested with a 1% saline solution. The results obtained were:

| Example 18 | 6.5 g/g |
|---|---|
| Example 19 | 6.0 g/g |
| Example 20 | 7.6 g/g |

By comparison, the absorbency of a similar tampon formed from a 100% "GALAXY" carded web in this test is 5.1 g/g.

EXAMPLES 21 and 22

The fibres produced in Example 15 were blended with fluffed wood pulp (a mixture of the pulps sold under the Trade Marks SAPPI diapers and CAIMA diapers for use in diapers) in different ratios. Such blends of wood pulp and absorbent material are used commercially in light-weight diapers. The absorbency of the blends in terms of free swell in 0.9% saline solution and retention after application of pressure was measured. As a comparison, sodium carboxymethyl cellulose (CMC) powder sold under the Trade Mark COURLOSE powder (having the highest absorption level amongst commercial CMC powders) was blended with the same wood pulp in the same ratios. The results obtained were:

| Example No. | Ratio of CMC fibres to wood pulp | Free Swell Absorbency g/g | Retention g/g | Comparative Results using CMC powder Free Swell g/g | Comparative Results using CMC powder Retention g/g |
|---|---|---|---|---|---|
| 21 | 15:85 | 22 | 12 | 20 | 12 |
| 22 | 50:50 | 34 | 25 | 23 | 16 |
| — | 0:100 | 12 | 8 | | |

As shown by these results, the carboxymethylcellulose fibres according to the invention increased absorbency by a similar amount to the CMC powder when used at the 15% level, but provided a much greater absorbency when used at the 50% level.

EXAMPLE 23

A solution of 6.5% sodium hydroxide and 19.2% sodium monochloroacetate was prepared and cooled to −2° C. in a treatment bath. A tow of never-dried TENCEL (1.7 decitex) was passed at 5 m/min successively through a roller nip of 100 kPa (to reduce the water content to 62% based on dry tow), the above treatment bath, a roller nip of 34 kPa (to give a total solution pick-up of 75%) and a drying cabinet at 90° C./10% RH for 7 minutes. The treated tow was washed as described in Example 11 and was re-dried and cut into staple.

The fibre produced had a degree of substitution above 0.1, a free swell absorbency in 0.9% saline solution of 34.1 g/g with a retention of 24.4 g/g, and a tenacity above 10 cN/tex. Fibre of this absorbency could be produced continuously if the temperature of the treatment bath was maintained at around 0° C., but the absorbency properties of the fibre produced fell slightly over time if the temperature of the treatment bath was allowed to rise.

We claim:

1. Carboxymethylated solvent-spun cellulose fibre having a degree of substitution of from 0.2 to 0.5 carboxymethyl group per glucose unit, an absorbency of at least 30 grams of a 0.9% saline solution per gram of fibre as measured by the free swell method and a tenacity of at least 10 cN/tex.

2. The fibre according to claim 1, wherein said absorbency is between 30 and 40 grams of a 0.9% saline solution per gram of fibre as measured by the free swell method.

3. The fibre according to claim 1, wherein said tenacity is from 15 to 25 cN/tex.

4. An absorbent personal product comprising at least one absorbent layer consisting essentially of a mixture of (a) between 10 to 50% by weight of a first textile fibre, which is a carboxymethylated solvent-spun cellulose fibre having a degree of substitution of from 0.2 to 0.5 carboxymethyl group per glucose unit, an absorbency of at least 30 grams of a 0.9% saline solution per gram of fibre as measured by the free swell method, and a tenacity of at least 10 cN/tex, and (b) between 90% and 50% by weight of at least one second textile fibre.

5. The product according to claim 4 wherein said second textile fibre is a cellulosic fibre.

6. An absorbent personal product comprising at least one absorbent layer consisting essentially of a mixture of between 10 and 50% by weight of absorbent fibre and between 50% and 90% by weight of fluffed wood pulp, wherein said absorbent fibre comprises carboxymethylated solvent-spun cellulose fibre having a degree of substitution of from 0.2 to 0.5 carboxymethyl group per glucose unit, an absorbency of at least 30 grams of a 0.9% saline solution per gram of fibre as measured by the free swell method, and a tenacity of at least 10 nN/tex.

7. A process for producing carboxymethyl cellulose fibre, said process comprising the steps of wetting solvent-spun cellulose fibre with a solution comprising an alkali metal hydroxide selected from the group consisting of sodium hydroxide and potassium hydroxide, and a monochloroacetic reagent selected from the group consisting of monochloroacetic acid and a monochloroacetate salt thereof, and heating said fibre in the presence of said solution at a temperature of at least 50° C. to provide a reaction between said solvent-spun cellulose fibre and the alkali metal hydroxide and the monochloroacetic reagent in said solution, said process producing carboxymethyl cellulose fibre having a degree of substitution of from 0.2 to 0.5 carboxymethyl group per glucose unit and an absorbency of at least 30 grams of a 0.9% saline solution per gram of fibre as measured by the free swell method.

8. The process according to claim 7, wherein said solvent-spun cellulose fibre is in tow or staple fibre form.

9. The process according to claim 7, wherein said solvent-spun cellulose fibre is never-dried fibre.

10. The process according to claim 7, wherein said solvent spun cellulose fibre is in the form of a woven, knitted or non-woven fabric.

11. The process according to claim 7, wherein said solution comprises an aqueous solution containing from 4 to 10% by weight of said alkali metal hydroxide and from 10 to 25% by weight of said monochloroacetate salt.

12. The process according to claim 7, wherein said wetting step comprises wetting solvent-spun cellulose fibre with said solution by padding; and said heating step comprises heating said fibre and solution to a temperature between 80° and 150° C.

13. The process according to claim 7, further comprising the steps of mixing said alkali metal hydroxide and said monochloroacetic reagent in solution at a temperature of 20° C. or below to form said solution of alkali metal hydroxide and monochloroacetic reagent; and maintaining said mixed solution at a temperature of 20° C. or below prior to said wetting step.

14. The process according to claim 7 wherein said wetting step comprises immersing the solvent-spun cellulose fibre in a mixed solution of the alkali metal hydroxide and the monochloroacetic reagent at a temperature of between 50° C. to the boiling point of said solution.

15. The process according to claim 7, wherein said wetting step further comprises wetting the solvent-spun cellulose fibre with a solution of said alkali metal hydroxide and said monochloroacetic reagent in a solvent mixture of water and a polar organic solvent.

16. A process for producing carboxymethyl cellulose fibre, said process comprising the steps of wetting solvent-spun cellulose fibre with a first solution of an alkali metal hydroxide selected from the group consisting of sodium hydroxide and potassium hydroxide and separately with a second solution of a monochloroacetate salt, and heating the wetted fibre to a temperature between 80° and 150° C. after it has been wetted with both said solutions, said process producing carboxymethyl cellulose fibre having a degree of substitution of from 0.2 to 0.5 carboxymethyl group per glucose unit and an absorbency of at least 30 grams of a 0.9% saline solution per gram of fibre as measured by the free swell method.

* * * * *

UNITED STATES PATENT AND TRADEMARK OFFICE
CERTIFICATE OF CORRECTION

PATENT NO. : 5,731,083
DATED : March 24, 1998
INVENTOR(S) : Hardev Singh Bahia and Jim Robert James It is certified that error appears in the above-indentified patent and that said Letters Patent is hereby corrected as shown below:

Col. 1, line 31, replace "736714" with -- 1736714 --.

Col. 4, line 9, replace "Just" with -- just --.

Col. 5, line 34, replace "hydrophiltc" with -- hydrophilic --.

Col. 6, line 61, insert a space between the words "formwhen".

Col. 7, line 5, replace "carboxymsuch acellulose" with -- carboxymethyl cellulose --.

Col. 7, line 66, replace "monochLoroacetate" with -- monochloroacetate --.

Col. 10, line 18, insert a space between the words "RHwas".

Col. 11, lines 62-63, delete the words "for use in diapers".

Col. 12, line 37, after "TENCEL", insert -- filaments --.

Signed and Sealed this

Eleventh Day of August 1998

Attest:

BRUCE LEHMAN

*Attesting Officer*   *Commissioner of Patents and Trademarks*